United States Patent [19]
Di Fiore et al.

[11] Patent Number: 5,810,842
[45] Date of Patent: Sep. 22, 1998

[54] EQUIPMENT FOR MICRODERMOABRASION THROUGH A FLOW OF AN AIR/REDUCING SUBSTANCES MIX

[75] Inventors: Dario Di Fiore; Carlo Stanisci, both of Florence, Italy

[73] Assignee: Mattioli Engineering S.R.L., Florence, Italy

[21] Appl. No.: 496,470

[22] Filed: Jun. 29, 1995

[30] Foreign Application Priority Data

Jun. 29, 1994 [IT] Italy ................................. FI94A0131

[51] Int. Cl.⁶ ............................................. A61B 17/50
[52] U.S. Cl. ............................................. 606/131; 606/167
[58] Field of Search ................................. 606/1, 131, 167, 606/159; 604/35

[56] References Cited

U.S. PATENT DOCUMENTS

| | | | |
|---|---|---|---|
| 5,037,431 | 8/1991 | Summers et al. | 606/131 |
| 5,037,432 | 8/1991 | Molinari | 606/131 |
| 5,100,412 | 3/1992 | Rosso | 606/131 |

FOREIGN PATENT DOCUMENTS 1 184 922  10/1987  Italy.

*Primary Examiner*—Glenn K. Dawson
*Attorney, Agent, or Firm*—Foley & Lardner

[57] ABSTRACT

A device for microdermoabrasion using a flow of a mixture of air and reducing substances, the device comprising a casing with a vacuum pump and a compressor at an interior of the casing. The device further comprising a control footswitch for actuating the compressor, a mixing bulb and a collecting bulb at an exterior of the casing, and a handpiece extending between the mixing bulb and the collecting bulb. The mixing bulb contains a mixture of air and reducing substances. The mixing bulb, the handpiece and the collecting bulb are monoblocks and are contained in a single cylinder block which is detachably connected to the casing.

10 Claims, 3 Drawing Sheets

FIG. 7
FIG. 8
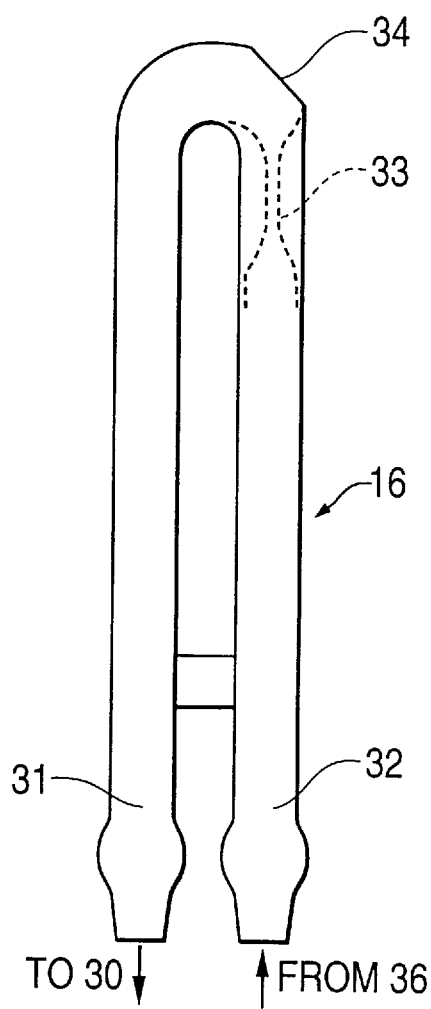
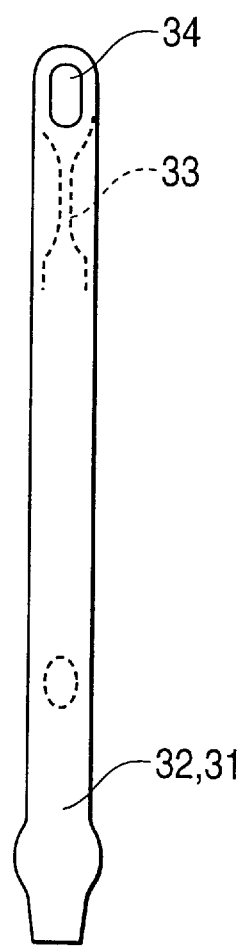

EQUIPMENT FOR MICRODERMOABRASION THROUGH A FLOW OF AN AIR/REDUCING SUBSTANCES MIX

FIELD OF THE INVENTION

This invention relates to a device for microdermoabrasion. More particularly, this invention relates to surgical equipment with a handpiece for microdermoabrasion on human tissue using a flow of reducing substances (e.g. corundum crystals).

BACKGROUND OF THE INVENTION

Prior art equipment for microdermoabrasion present considerable drawbacks:

1) Formation of bacterial sacs is difficult to eliminate.
2) Obstruction of the flow of air and reducing substances that causes the equipment to become blocked.

These drawbacks are in large part a result of the configuration of the handpiece.

It is known in the prior art of equipment and handpieces to effect localized operations of microdermoabrasion through a flow of a mixture of air and reducing substances.

For example, European Patent Application No. EP-A-0 324 448 discloses equipment for human epidermis microdermoabrasion which comprises a handpiece having an entrance and an exit pipe which share an opening that may be placed on the surface to be treated. The equipment further comprises a pneumatic supply of reducing substances. The equipment is characterized by supplying means which includes a vacuum, and the entrance pipe is connected to a container where reducing substances are found. The container is provided with a large number of entrance holes for providing air. Some of the entrance holes have associated valves. Air and reducing substances are mixed within the container.

Even if this equipment resolves the problem of obstruction of flow, it does not solve an additional problem of needing easy sterilization. Sterilization would involve disassembly of the whole system by a specialized technician, which is not a reasonable procedure.

European Patent Application No. EP-A-0 318 042 discloses equipment with a handpiece for microdermoabrasion. The equipment includes a device for air compression and also a vacuum.

The mixture of air and reducing substances goes through a nozzle inside of the handpiece and is turned towards an exit window, and is then projected onto an area of skin to be treated. The handpiece is assembled from multiple components, which entails a considerable production cost. All components of the handpiece, to avoid corrosion, are manufactured from special materials, for example tungsten steels, or WIDIA®. For other handpieces of this kind, it has been suggested that the head, in which the window extends for application to the skin, should be advantageously manufactured from a disposable material, for instance polycarbonate.

The equipment of European Patent Application No. EP-A-0 318 042 does not solve the problem of allowing sterilization with a reasonable procedure. The equipment uses a pneumatic system called "reversing air flux", that does not always act in an efficaciously way and that worsens the hygienic problem of bacterial sac formation. In trying to avoid disassembly it is useful to effect air flow at the interior of the pipes in a direction opposite the normal work direction of the mixture of air and reducing substances. However this operation may cause abraded tissue to pollute the container of reducing material, which will be in contact with the future patient's skin and potentially have negative implications. The above-mentioned obstructions often occur at the handpiece level.

SUMMARY OF THE INVENTION

The present invention uses new conception components, particularly tempered pyrex glass, to allow ease of manufacture and simplification of equipment sterilization. Sterilization of the parts that have been in contact with human tissue particles may be effected with different techniques, for example in an autoclave or under UV rays. These parts may be sterilized quickly and may be replaced in a few seconds by appropriate spare-parts supplied with the equipment. This operation may be executed by an unspecialized operator.

The present invention includes a handpiece that may be used, after suitable changes, on other equipment for microdermoabrasion. In particular, the handpiece described may be advantageously used with the equipment of the present invention, which is usable in applications of traditional microdermoabrasion, for example:

acne scars;
light wrinkles and long sun exposure wrinkles;
disfiguring scars;
stretch marks;
hyperpigmentation;
tatoos;
burns.

A lightweight handpiece, as provided by the present invention, allows increased maneuverability in executing the treatments and a better operative sensitivity. The sliding of the handpiece over a surface of the skin occurs in a soft and regular way. Due to the geometry of the handpiece, the deposit of crystals on the patients' skin is reduced. Also, faster and easier cleaning of the parts in comparison to the traditional metallic handpieces is achieved.

The geometry of the handpiece and the materials used for the components eliminate or make almost negligible any obstruction of the handpiece. In particular, the low friction value between the reducing crystals and the pyrex glass, the particular structure of the handpiece (a monoblock without sharp jutting corners, or edges along the passage in which the crystals flow), the placement of the nozzle, the way the nozzle is connected to the rest of the handpiece, and the simple and efficacious mixture of air and reducing crystals leaves this equipment free from obstructions.

If an obstruction occurs, due for example to wide impurities in the reducing material, the obstruction would be immediately localized by a simple check of the handpiece and of the mixing container. The transparent material of the handpiece and mixing container allow immediate identification of the obstruction.

It is then possible to quickly replace the obstructed component and continue the treatment. Once separated from the rest of the equipment, the obstructed component can be unclogged by a light flow of compressed air or by washing with water.

The above-mentioned advantageous handpiece of the present invention has an industrial cost which is 10 times less than that of traditional metallic handpieces.

"Monoblock" is defined as a constructive component of the equipment composed of one or more integral parts, without the use of mobile mechanical connections and without it being possible to split the component up into multiple subparts.

BRIEF DESCRIPTION OF THE DRAWINGS

The accompanying drawings, which are incorporated in and constitute a part of the specification, illustrate a presently preferred embodiment of the invention, and, together with the general description of the preferred embodiment given below, serve to explain the principles of the invention.

FIG. 7 is a front view of a handpiece of the present invention; and

FIG. 8 is side view of the handpiece of FIG. 7.

DETAILED DESCRIPTION OF THE PREFERRED EMBODIMENT

Figure 1:
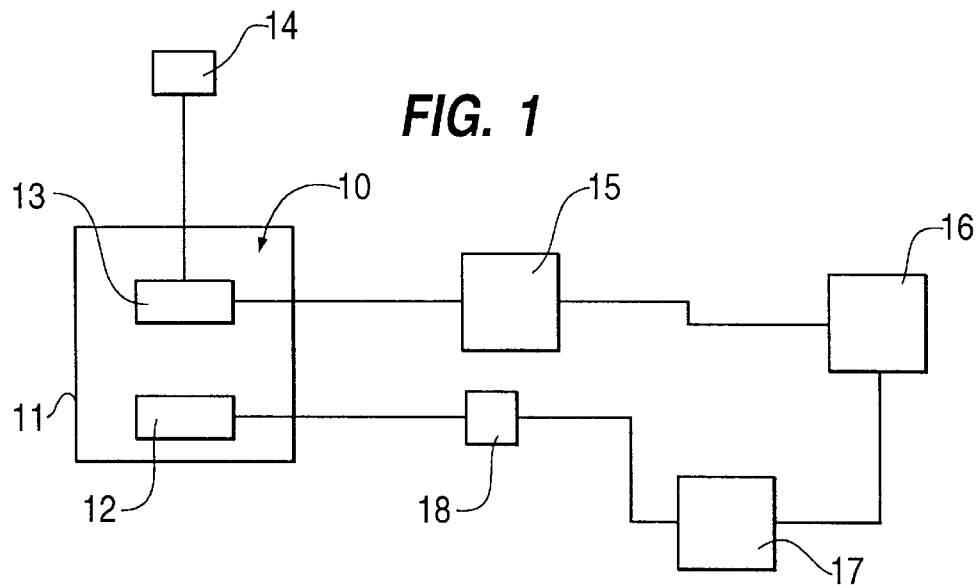
FIG. 1 is a schematic block diagram of equipment according to the present invention.

The present invention includes equipment for microdermoabrasion using a flow of a mixture of air and reducing substances, comprising a casing (11) in which a vacuum pump (12) is placed and a compressor (13) is actuated by a control footswitch (14). The equipment further comprises a mixing bulb (15) containing a mixture of air and reducing substances, a handpiece (16), and a collecting bulb (17). The mixing bulb (15), the handpiece (16) and the collecting bulb (17) are contained in one cylinder block. The handpiece (16) is connected to the mixing bulb (15) by a first conduit, and to the collecting bulb (17) by a second conduit.

The schematic block diagram of FIG. 1 represents the general architecture of the equipment for microdermoabrasion, according to the present invention. The equipment comprises a body machine (10), composed of an external casing (11) which has at its interior a vacuum pump (12), a compressor (13) with a control footswitch (14), and adjusting and control devices (not shown in FIG. 1). The equipment further comprises a mixing bulb (15) containing reducing materials (in particular corundum crystals), a handpiece (16), a collecting bulb (17) and a feedback air filter (18).

The steps to be performed by an operator on traditional equipment or on equipment of the present invention, are the following:

a) Switching "ON" of the equipment and initially adjusting the vacuum level desired.

b) Positioning the handpiece (16) on the area to be treated.

C) Actuating the compressor (13) through the footswitch (14) if a deep abrasion is required.

Figure 6:
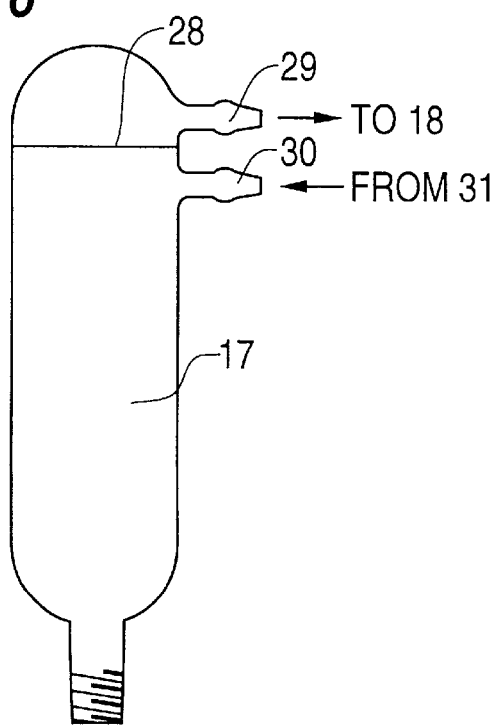
FIG. 6 is a side view of a collecting bulb.

When the operator puts a small window of the handpiece in contact with an area of the skin to be treated, air will be mixed with the reducing crystals in the mixing bulb (15) due to the vacuum created. The mixture is then sent with a strong kinetic energy through the handpiece nozzle. When exposed to the skin tissue to be treated, the reducing crystals abrade the patient's skin, and the mixture of air and reducing materials with the removed skin fragments is vacuumed into the collecting bulb (17). At a bottom of the collecting bulb (17), crystals and tissue fragments are deposited. A porous septum (28) (comprising, for example, sintered glass) of the collecting bulb (17) (see FIG. 6), separates the vacuum pipe (29) from the crystal return pipe (30). The porous septum (28) does not allow the reducing material mixed with the skin fragments to reach an impeller of the vacuum pump (12). Safety filtering is effected through a feedback air filter (18) placed downstream from the collecting bulb (17). The filter (18) does not allow the skin fragments, which escape into the sintered glass porous septum (28) from the collecting bulb, to enter the body machine (10). Entry of the skin fragments into the body machine (10) would cause a potential risk of bacterial sacs. The feedback air filter (18) may be periodically easily replaced without disassembly, since the capsule containing the feedback air filter (18) is accessible from an external part of the equipment.

Figure 2:
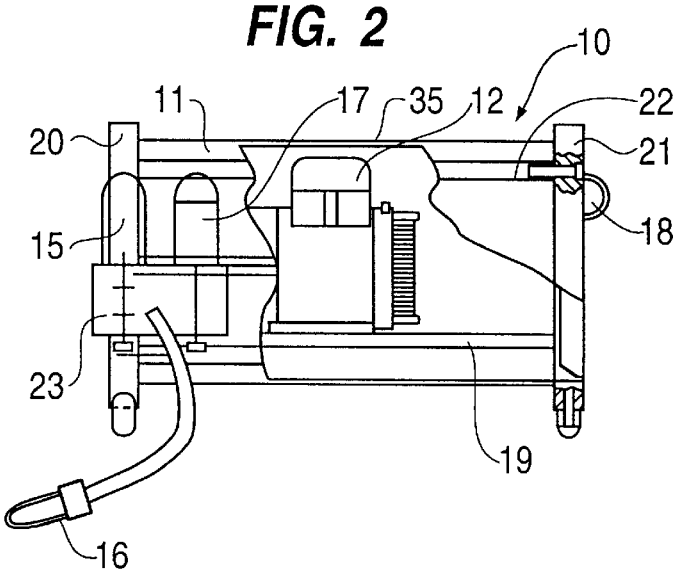
FIG. 2 is a side view of the equipment of the present invention.
Figure 3:
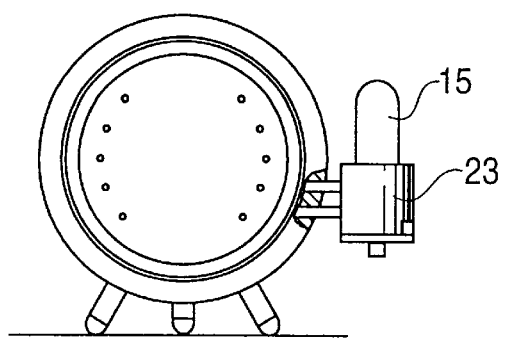
FIG. 3 is front view of the equipment of the present invention.

It is evident from FIGS. 2 & 3, that the casing (11) comprises of a cylindrical case (35), for example made from Plexiglass, of a support beam (19). The vacuum pump (12) and the compressor (13) are supported by the support beam (19). The casing further comprises two side flanges (20, 21) held together by several threaded connecting-rods (22). The front flange (20) supports a small tumbler (23), which supports the mixing bulb (15) and the collecting bulb (17). The rear flange (21) supports the feedback air filter (18). The mixing bulb (15) (see FIGS. 4 & 5), besides containing reducing substances ready to use, contains a mixture of air and reducing substances. It comprises a single element in a glass or plastic material.

Using tempered pyrex glass for the mixing bulb (15) has advantageous results. The combination of air and reducing substances is optimally predetermined by the crystal vacuum hole (26) placed in the lower part of the mix cannula (24). The air is vacuumed from an exterior of the mixing bulb (15) through a closing cap (27) of the mixing bulb (15), which comprises an appropriate lining of sintered glass. The air vacuumed from the bulb exterior may enter the upper opening of the mix cannula (24), and in its flow drag the reducing substances present inside the mixing bulb (15) to be vacuumed through the vacuum hole (26). The mixing bulb (15) includes two pipes (25, 36) and the closing cap (27) for filling the mixing bulb (15) with the reducing substances. The cap (27) is supplied with a sintered glass lining of appropriate porosity to allow entrance of a necessary amount of air for the mix. The cap (27) simultaneously lets air in and retains the reducing materials. The two pipes (36, 25) correspond, respectively, to the connecting pipe that directs the mixture of air and reducing substances toward the handpiece (16), and the connecting pipe which carries a compressed air flow in an interior of the mixing bulb (15). The air flow is generated by the compressor (13), and is controlled by the footswitch (14). The air flow is required to impart a higher kinetic energy to the reducing material for a stronger power of abrasion.

Figure 4:
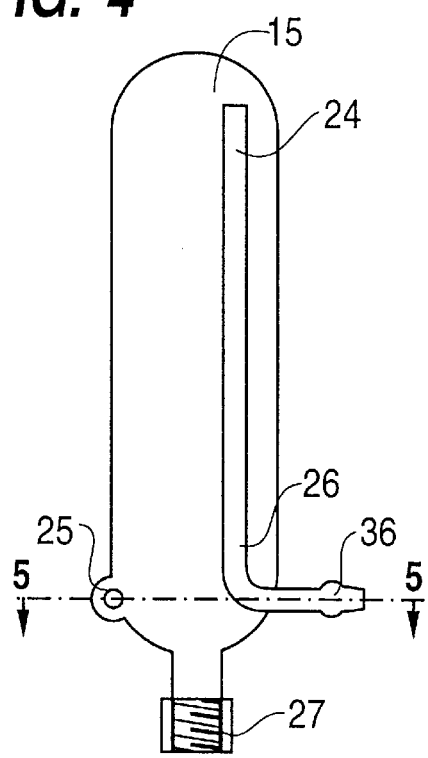
FIG. 4 is a side view of a mixing bulb.
Figure 5:
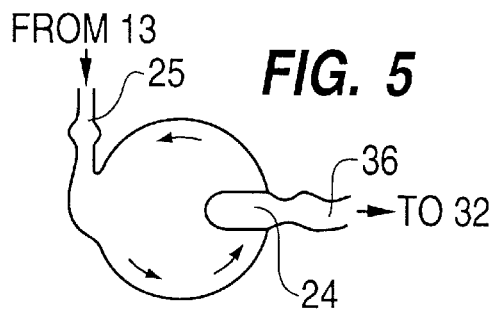
FIG. 5 is a cross section of the mixing bulb of FIG. 4, taken along section A—A of FIG. 4.

In a preferred embodiment of the invention, the flow of compressed air may be directed to the interior of the mixing bulb (15) according to a direction tangential to the mixing bulb's wall (see FIGS. 4 & 5). In this way, the reducing substances act according to directions concentric to the main symmetrical axis of the mixing bulb (15), thus obtaining a substantial kinetic energy before entering the vacuum hole (26). This method of mixing of air with reducing substances creates an improved abrasive action.

The bulbs (15, 17) are releasably supported by the tumbler (23). This allows, when necessary, an immediate replacement of the bulbs (15, 17). In fact, it is enough to disconnect the pipes and pull out the two bulbs (15), (17) from the tumbler (23).

As consequence of the vacuum being applied to the exit pipe (31), the mixture of air and reducing material is drawn into the entrance of the mix arrival pipe (32).

In an interior of the handpiece (16), the mixture gains considerable speed going through the nozzle (33) (e.g. a Venturi pipe) placed at an upper part of the handpiece (16). As shown in FIGS. 7 & 8, the reducing materials discharge most of their kinetic energy contacting the area of skin to be treated, which "closes" an exit window (34). After having executed the abrasive operation, the mixture of air and reducing materials, which contains some skin fragments, is evacuated through the exit pipe (31) toward the collecting bulb (17). The handpiece (16) can be made by folding a pipe (e.g. comprising tempered pyrex glass) into a U-shape. The elliptic shaped exit window (34), is placed after folding the pipe, in front of the nozzle (33) and may be raked at an angle between 30° and 60°, respectively, to a central symmetrical axis of the handpiece (16).

Advantageously, the relation between length and diameter of a groove of the nozzle (33), and between a length of the handpiece (16) and a diameter of the handpiece pipe, should be between 5 and 30.

The composition of tempered pyrex glass and the geometry of the handpiece (16) allow, together with the handpiece lightness, increased maneuverability to treat the skin and increased operative sensitivity. The handpiece (16) sliding over the skin occurs in a soft and regular way. Due to the geometry of the handpiece (16) and the exit window (34), the regeneration of reducing substances is almost total and consequently their deposit on the skin after the treatment is much reduced. This fact allows a simple and fast cleaning of the treated part.

Other embodiments of the microdermoabrasion equipment will be apparent to those skilled in the art from consideration of the specification disclosed herein. It is intended that the specification be considered as exemplary only, with the true scope and spirit of the invention being indicated by the following claims.

Italian Patent Application No. FI/94/A/131 is incorporated herein by reference in its entirety.

What is claimed is:

1. A device for microdermoabrasion using a flow of a mixture of air and a reducing substance, the device comprising:

a casing;

a vacuum pump at an interior of the casing;

a compressor at an interior of the casing;

a control footswitch operatively connected to the compressor for actuating the compressor;

a mixing bulb at an exterior of the casing;

a collecting bulb at an exterior of the casing; and a handpiece extending between the mixing bulb and the collecting bulb;

wherein the mixing bulb contains a mixture of air and reducing substances; and wherein the mixing bulb, the handpiece and the collecting bulb each comprise a single monoblock and together form a single unit which is detachably connected to the casing.

2. A device as claimed in claim 1, wherein the mixing bulb, the handpiece and the collecting bulb comprise a glass material.

3. A device as claimed in claim 2, wherein the glass material comprises at least one of pyrex and sintered glass.

4. A device as claimed in claim 1, wherein the mixing bulb, the handpiece and the collecting bulb comprise a plastic material.

5. A device as claimed in claim 1, wherein the casing comprises a cylindrical plexiglass case, a support beam and two side flanges;

wherein the vacuum pump and the compressor are supported by the support beam; and wherein the two side flanges are held together by at least one threaded connecting rod.

6. A device as claimed in claim 1, further comprising a feedback air filter connected to an exterior of the casing.

7. A device as claimed in claim 1, wherein the mixing bulb is a monoblock comprising:

an external case;

a mix cannula having at least one vacuum hole; and a compressed air emission pipe extending tangential with respect to the external case.

8. A device as claimed in claim 7, further comprising at least one cap having a sintered glass lining enclosing a tip of the air emission pipe.

9. A device as claimed in claim 1, further comprising a porous septum of sintered glass at an interior of the collecting bulb which separates a vacuum pipe of the collecting bulb from a crystal return pipe of the collecting bulb.

10. A device as claimed in claim 1, further comprising a tumbler having two sections and being located at an exterior of the casing, the tumbler supporting the mixing bulb and the collecting bulb.

* * * * *